US005308760A

United States Patent [19]

Brown et al.

[11] Patent Number: 5,308,760

[45] Date of Patent: May 3, 1994

[54] **CRYSTAL PROTEINS OF *BACILLUS THURINGIENSIS*, GENES ENCODING THEM, AND HOST EXPRESSING THEM**

[75] Inventors: Kit L. Brown, Vallejo, Calif.; Helen R. Whiteley, deceased, late of Seattle, Wash., by Arthur H. Whiteley, administrator

[73] Assignee: Washington Research Foundation, Seattle, Wash.

[21] Appl. No.: 828,700

[22] Filed: Feb. 3, 1992

Related U.S. Application Data

[63] Continuation-in-part of Ser. No. 817,915, Jan. 10, 1992, abandoned.

[51] Int. Cl.[5] ...................... C12P 21/06; C12N 15/00; C07H 15/00

[52] U.S. Cl. ................................ 435/69.1; 435/252.3; 435/252.8; 435/320.1; 536/23.71; 424/93 L

[58] Field of Search ............... 435/69.1, 252.5, 252.33, 435/320.1, 252.3, 252.8, 69.1; 935/6, 9, 72, 73; 536/27, 23.71; 424/93 L

[56] References Cited

U.S. PATENT DOCUMENTS

| | | | |
|---|---|---|---|
| 4,771,131 | 9/1988 | Herrnstadt et al. | 424/93 L |
| 4,996,155 | 2/1991 | Sick et al. | 435/69.1 |
| 5,039,523 | 8/1991 | Payne et al. | 424/93 L |

OTHER PUBLICATIONS

Perfontaine et al. Applied & Envir. Micb. vol. 53 12 pp. 2808-2814 Dec. 1987.
Kronstad et al. J. Bact. 154 (1) pp. 419-428 Apr. 1983.
Schnepf et al, J. Biol. Chem. 265 (34) pp. 20923-20930, Nov. 1990.
Widner et al. J. Bact. 172 (6) pp. 2826-2832 Jun. 1990.
M. Lynch et al., "Immunological Comparisons of the Crystal Protein from Strains of *Bacillus thuringiensis*," Journal of Invertebrate Pathology, 46, pp. 47-57 (1985).
Calabrese et al., "A Comparison of Protein Crystal Subunit Sizes in *Bacillus thuringiensis*," Can. J. Microbiol., vol. 26, pp. 1006-1010 (1980).

*Primary Examiner*—Robert A. Wax
*Assistant Examiner*—D. Schmickel
*Attorney, Agent, or Firm*—Wegner, Cantor, Mueller & Player

[57] ABSTRACT

Two genes encoding the predominant polypeptides of *Bacillus thuringiensis subsp. thompsoni* cuboidal crystals were cloned in *Escherichia coli* and sequenced. The new class of crystal proteins have electrophoretic mobilities of 40 and 34 kilodaltons (kDa) with the deduced amino-acid sequences predicting molecular masses of 35,384 and 37,505 daltons, respectively. No statistically significant similarities were detected for the 40 kDa and 34 kDa crystal proteins to any other characterized *Bacillus thuringiensis* crystal protein or to each other. A 100 MDa plasmid encodes both crystal protein genes, which appear to be part of an operon with the 40 kDa gene 64 nucleotides upstream of the 34 kDa gene. Both crystal proteins are synthesized in approximately the same amounts. Even though small, compared to other crystal proteins, the 34 kDa crystal protein has insecticidal activity against lepidopteran larvae (*Manduca sexta*).

20 Claims, 13 Drawing Sheets

```
  1 CCAATAAGGTGTCAGCTGAATCTAAATTCGAAAGGAGAATAAAAATGAATTTTAACAATATCAC
                                                   M  N  F  N  N  I  T
                                                 101

    AGGAAATTTAAAGATGTCACAGAACTATTTACAGATTACGCTAATCAATGGAGTCGGCAAAA
     G  N  F  K  D  V  T  E  L  F  T  D  Y  A  N  Q  W  S  R  Q  N

    TGGGGGTGGTAAGCCTGAAATTTCTCTTATAGTACCAGGGTATGAGGCTTATGCTGTGACTAG
     G  G  K  P  E  I  S  L  I  V  P  G  Y  E  A  Y  A  V  T  S
                                  201

    TTCTGATGATAGAACTATCTATCATCATCCAAAGAAAAAGAAACGAGAAAAATCGAGATCACA
     S  D  D  R  T  I  Y  H  H  P  K  K  K  K  R  E  K  S  R  S  H
```

FIG. 4A

```
                                                          301
TCATGGTTGCTCAAGCGAGAACCAGGAACGTATATATGAAGATACGTATGAGACTAATCTATC
 H  G  C  S  S  E  N  Q  E  R  I  Y  E  D  T  Y  E  T  N  L  S

TTTCAATCATGATCCTAATTTAATGGAAGAATGCGAAAAGGAAATTGAACTTGCAACTGAGAC
 F  N  H  D  P  N  L  M  E  E  C  E  K  E  I  E  L  A  T  E  T
                              401
GTATGAAAATGCCAGTTGTCATGAAAAGAAAATAAAGATACAAATCGGTGGAAATGTAGAAAA
 Y  E  N  A  S  C  H  E  K  K  I  K  I  Q  I  G  G  N  V  E  N
                                                                     501
TTATGGTGAGTGGTTCGTTTACGAAGGGGCAACTTTATCAGGAAAAGACCTTCTATCCATTGA
```

```
Y  G  E  W  F  V  Y  E  G  A  T  L  S  G  K  D  L  L  S  I  D

TGTATTTGGACATGAACCAGTAGACATTGATCAAGTCCCTGTTTCATTGCATCCAGGAGAAAT
V  F  G  H  E  P  V  D  I  D  Q  V  P  V  S  L  H  P  G  E  I
                              601
AGAAGTATTAAAGCGACCATTGGAAGTTGACACATATCGCTCTTATAAGATTCGCCCTCGTTC
E  V  L  K  R  P  L  E  V  D  T  Y  R  S  Y  K  I  R  P  R  S

TAAGGTCACTGCGACTTTGAAAGTAAAACAAAAACATTTTAAACAGTGCTTTGATGTGGAAAC
K  V  T  A  T  L  K  V  K  Q  K  H  F  K  Q  C  F  D  V  E  T
      701
AGATGTATCTGGTTATGTTGCAATTATACAAAAACAAAAAGATTGTGATGTACAGACATCATTTC
D  V  S  G  Y  V  A  I  I  Q  K  Q  K  D  C  D  V  Q  T  S  F  H
```

FIG. 4C

```
                                                801
ACCATGTTGCCGCTATTTTACAACGGTATTACAGTCCCTTTATTCGTATCAATGGAGATGAAGTA
 H  V  A  A  I  L  Q  R  Y  Y  S  P  F  I  R  I  N  G  D  E  V

ACTTTACTGTGTAAAGGAGTATTTAAAGGGGTTAAGATTACGGATATATATATTCATATCCAGATA
T  L  L  C  K  G  V  F  K  G  V  K  I  T  D  I  Y  I  H  I  Q  I
         901
GAAAGTTTAGATATTCCTGGATTGATTGAAGAGTATAACATTTATGATGTGAATCAACGAAATATA
E  S  L  D  I  P  G  L  I  E  E  Y  N  I  Y  D  V  N  Q  R  N  I
                                                    1001
GGTGTAATGGAATGATAGTACAAAACTCATAAATTAGATTGATGAGAATCTGATTTATATTTTAAA
G  V  M  E
```

FIG. 4D

```
GGAGGAATTTATAATGGCAATTATGAATGATATTGCACAAGATGCAGCAAGAGCTTGGGATATAAT

                 M  A  I  M  N  D  I  A  Q  D  A  A  R  A  W  D  I  I
                1101
AGCAGGGCCATTTATACGACCGGGAACAACTCCTACCAATCGACAATTATTTAATTATCAAATTG
 A  G  P  F  I  R  P  G  T  T  P  T  N  R  Q  L  F  N  Y  Q  I  G
                                                   1201
GAAATATAGAGGTTGAACCTGGAAATCTTAATTTTTCAGTCGTCCCTGAACTAGACTTTAGTGTC
  N  I  E  V  E  P  G  N  L  N  F  S  V  V  P  E  L  D  F  S  V

TCTCAAGACCTTTTCAACAATACAAGTGTGCAGCAAAGTCAAACAGCATCATTTAACGAATCAAG
 S  Q  D  L  F  N  N  T  S  V  Q  Q  S  Q  T  A  S  F  N  E  S  R
```

FIG. 4E

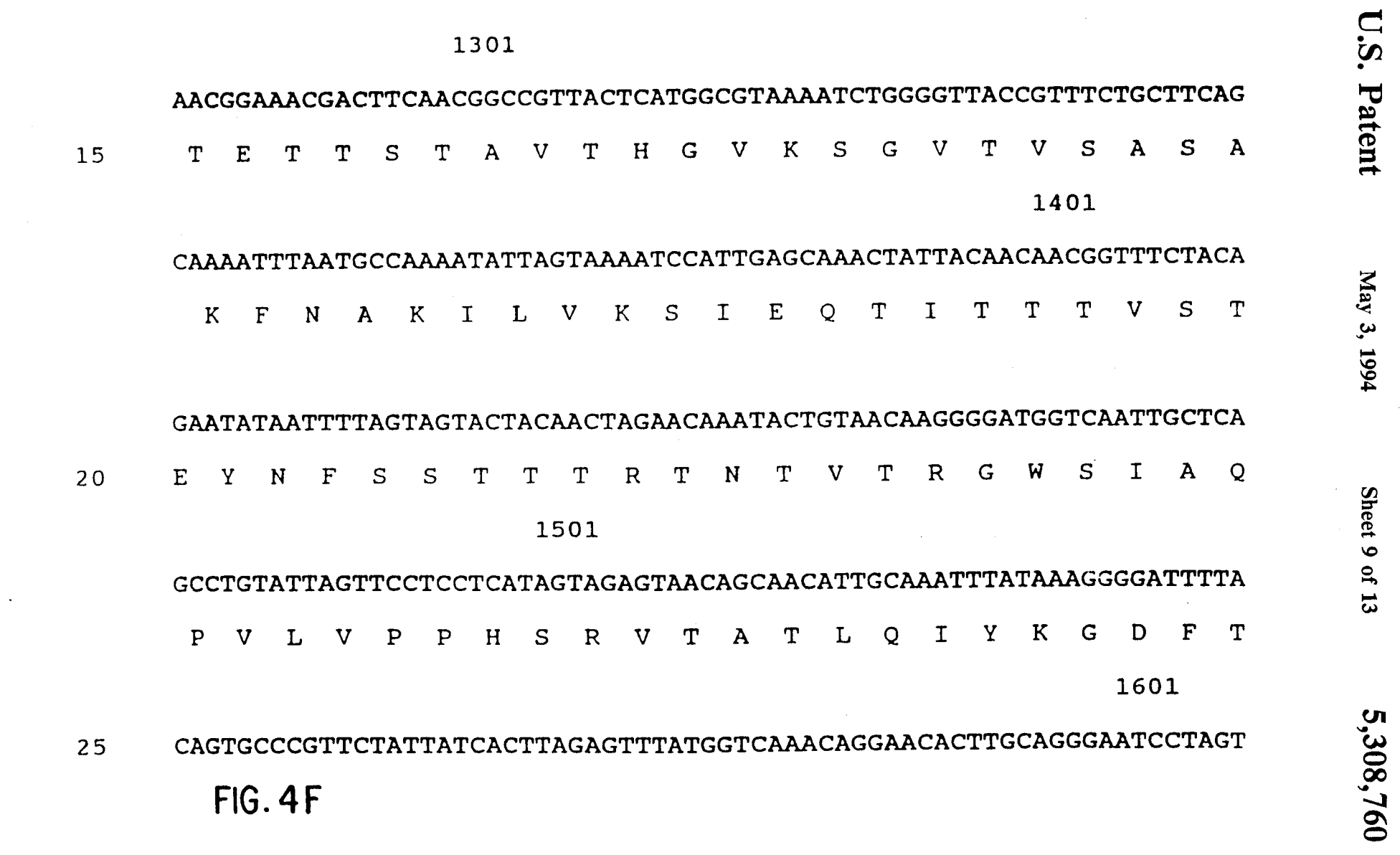

```
                    1301
AACGGAAACGACTTCAACGGCCGTTACTCATGGCGTAAAATCTGGGGTTACCGTTTCTGCTTCAG
 T  E  T  T  S  T  A  V  T  H  G  V  K  S  G  V  T  V  S  A  S  A
                                                          1401
CAAAATTTAATGCCAAAATATTAGTAAAATCCATTGAGCAAACTATTACAACAACGGTTTCTACA
  K  F  N  A  K  I  L  V  K  S  I  E  Q  T  I  T  T  T  V  S  T

GAATATAATTTTAGTAGTACTACAACTAGAACAAATACTGTAACAAGGGGATGGTCAATTGCTCA
E  Y  N  F  S  S  T  T  T  R  T  N  T  V  T  R  G  W  S  I  A  Q
                          1501
GCCTGTATTAGTTCCTCCTCATAGTAGAGTAACAGCAACATTGCAAATTTATAAAGGGGATTTTA
 P  V  L  V  P  P  H  S  R  V  T  A  T  L  Q  I  Y  K  G  D  F  T
                                                              1601
CAGTGCCCGTTCTATTATCACTTAGAGTTTATGGTCAAACAGGAACACTTGCAGGGAATCCTAGT
```

FIG. 4F

```
V  P  V  L  L  S  L  R  V  Y  G  Q  T  G  T  L  A  G  N  P  S
TTTCCTTCTTTATATGCAGCCACACATATGAAAACACACTTTTGGGAAGAATTAGAGAGCATATTGC
F  P  S  L  Y  A  A  T  Y  E  N  T  L  L  G  R  I  R  E  H  I  A
                              1701
TCCACCTGCTCTTTCAGAGCCTCCAACGCCATACATTCGAATGGCGTTCAGGCAATTTGGAGAG
P  P  A  L  F  R  A  S  N  A  Y  I  S  N  G  V  Q  A  I  W  R  G
                                                        1801
GAACAGCAACGACGAGAGTTTCGCAAGGTCTCGTTATTCCGTTGTAAGAATCGATGAAAGACCTTTA
T  A  T  T  R  V  S  Q  G  L  Y  S  V  V  R  I  D  E  R  P  L
GCAGGTTATTCAGGAGAAACAAGAACGTATTATTACCAGTGACACTTTCAAATTCAAGTCAAAT
A  G  Y  S  G  E  T  R  T  Y  Y  L  P  V  T  L  S  N  S  S  Q  I
```

1901

CCTTACACCTGGTTCTTTAGGAAGTGAGATTCCAATTATCAATCCAGTTCCGAATGCATCTTGTA

L T P G S L G S E I P I I N P V P N A S C K

AAAAGGAAAACTCGCCTATTATCATTCATCATGATCGAGAGAAGCATCGTGAACGCGATTATGA

K E N S P I I I H H D R E K H R E R D Y D

2001

TAAAGAGCATATTTGTCATGATCAAGCTGAGAAGTATGAACGCGATTATGATAAAGAATAACTAA

TTATGTAAGAGATTTGTAAACAAGAGAAATAGCATTTTACTATTTCTCTTGTTTTTAATCTATAT

> <

ATAGAATGGTAGACGCTCTTTAAATTAAATGTAAAAAAAGGGGGCTAAGATTATAATGAAATCAA

2201

ATCCAAAACAATATATAGCTAATTATTTTACTTCTTTTTCATGTATTGGTCCGGATTGTGAAGATCA

FIG. 4I

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: thompsoni ( i x ) FEATURE:
( A ) NAME/KEY: modifiedbase
( B ) LOCATION: 20..21
( C ) IDENTIFICATION METHOD: experimental
( D ) OTHER INFORMATION: /evidence=EXPERIMENTAL
/ modbase=i ( i x ) FEATURE:
( A ) NAME/KEY: modifiedbase
( B ) LOCATION: 22..23
( C ) IDENTIFICATION METHOD: experimental
( D ) OTHER INFORMATION: /evidence=EXPERIMENTAL
/ modbase=i ( x i ) SEQUENCE DESCRIPTION: SEQ ID NO:1:

ATGAAYTTCA ACAAYATYAC GGAACTTYAA GGACGT 36

( 2 ) INFORMATION FOR SEQ ID NO:2:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( i x ) FEATURE:
( A ) NAME/KEY: modifiedbase
( B ) LOCATION: 14..15
( C ) IDENTIFICATION METHOD: experimental
( D ) OTHER INFORMATION: /evidence=EXPERIMENTAL
/ modbase=i ( i x ) FEATURE:

-continued ( A ) NAME/KEY: modifiedbase
( B ) LOCATION: 22..23
( C ) IDENTIFICATION METHOD: experimental
( D ) OTHER INFORMATION: /evidence=EXPERIMENTAL
/ modbase=i ( i x ) FEATURE:
( A ) NAME/KEY: modifiedbase
( B ) LOCATION: 24..25
( C ) IDENTIFICATION METHOD: experimental
( D ) OTHER INFORMATION: /evidence=EXPERIMENTAL
/ modbase=i ( i x ) FEATURE:
( A ) NAME/KEY: modifiedbase
( B ) LOCATION: 26..27
( C ) IDENTIFICATION METHOD: experimental
( D ) OTHER INFORMATION: /evidence=EXPERIMENTAL
/ modbase=i ( x i ) SEQUENCE DESCRIPTION: SEQ ID NO:2:

ATGAATGAYA TWGCCARGAT GCGCMGGC 28

( 2 ) INFORMATION FOR SEQ ID NO:3:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( x i ) SEQUENCE DESCRIPTION: SEQ ID NO:3:

GAGGGCCCAA TAAGGTGTCA GCT 23

( 2 ) INFORMATION FOR SEQ ID NO:4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( x i ) SEQUENCE DESCRIPTION: SEQ ID NO:4:

GCGTCGACTA TCATTCCATT ACAC 24

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( x i ) SEQUENCE DESCRIPTION: SEQ ID NO:5:

CTCCCGGGTG TAATGGAATG ATA 23

( 2 ) INFORMATION FOR SEQ ID NO:6:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( x i ) SEQUENCE DESCRIPTION: SEQ ID NO:6:

GCTCTAGATC TTCACAATCC GGA 23

( 2 ) INFORMATION FOR SEQ ID NO:7:

( i ) SEQUENCE CHARACTERISTICS:
( A ) LENGTH: 2259 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: thompsoni ( x i ) SEQUENCE DESCRIPTION: SEQ ID NO:7:

CCAATAAGGT GTCAGCTGAA TCTAAATTCG AAAGGAGAAT AAAAATGAAT TTTAACAATA 60

TCACAGGAAA TTTTAAAGAT GTCACAGAAC TATTTACAGA TTACGCTAAT CAATGGAGTC 120

GGCAAAATGG GGGTGGTAAG CCTGAAATTT CTCTTATAGT ACCAGGGTAT GAGGCTTATG 180

CTGTGACTAG TTCTGATGAT AGAACTATCT ATCATCATCC AAAGAAAAAG AAACGAGAAA 240

AATCGAGATC ACATCATGGT TGCTCAAGCG AGAACCAGGA ACGTATATAT GAAGATACGT 300

ATGAGACTAA TCTATCTTTC AATCATGATC CTAATTTAAT GGAAGAATGC GAAAAGGAAA 360

TTGAACTTGC AACTGAGACG TATGAAAATG CCAGTTGTCA TGAAAAGAAA ATAAAGATAC 420

AAATCGGTGG AAATGTAGAA AATTATGGTG AGTGGTTCGT TTACGAAGGG GCAACTTTAT 480

CAGGAAAAGA CCTTCTATCC ATTGATGTAT TTGGACATGA ACCAGTAGAC ATTGATCAAG 540

TCCCTGTTTC ATTGCATCCA GGAGAAATAG AAGTATTAAA GCGACCATTG GAAGTTGACA 600

CATATCGCTC TTATAAGATT CGCCCTCGTT CTAAGGTCAC TGCGACTTTG AAAGTAAAAC 660

AAAAACATTT TAAACAGTGC TTTGATGTGG AAACAGATGT ATCTGGTTAT GTTGCAATTA 720

TACAAAAACA AAAAGATTGT GATGTACAGA CATCATTTCA CCATGTTGCC GCTATTTTAC 780

AACGGTATTA CAGTCCCTTT ATTCGTATCA ATGGAGATGA AGTAACTTTA CTGTGTAAAG 840

GAGTATTTAA AGGGGTTAAG ATTACGGATA TATATATTCA TATCCAGATA GAAAGTTTAG 900

ATATTCCTGG ATTGATTGAA GAGTATAACA TTTATGATGT GAATCAACGA AATATAGGTG 960

TAATGGAATG ATAGTACAAA ACTCATAAAT TAGATTGATG AGAATCTGAT TTATATTTTA 1020

AAGGAGGAAT TTATAATGGC AATTATGAAT GATATTGCAC AAGATGCAGC AAGAGCTTGG 1080

GATATAATAG CAGGGCCATT TATACGACCG GGAACAACTC CTACCAATCG ACAATTATTT 1140

AATTATCAAA TTGGAAATAT AGAGGTTGAA CCTGGAAATC TTAATTTTTC AGTCGTCCCT 1200

GAACTAGACT TTAGTGTCTC TCAAGACCTT TTCAACAATA CAAGTGTGCA GCAAAGTCAA 1260

ACAGCATCAT TTAACGAATC AAGAACGGAA ACGACTTCAA CGGCCGTTAC TCATGGCGTA 1320

AAATCTGGGG TTACCGTTTC TGCTTCAGCA AAATTTAATG CCAAAATATT AGTAAAATCC 1380

ATTGAGCAAA CTATTACAAC AACGGTTTCT ACAGAATATA ATTTTAGTAG TACTACAACT 1440

-continued

```
AGAACAAATA CTGTAACAAG GGGATGGTCA ATTGCTCAGC CTGTATTAGT TCCTCCTCAT 1500
AGTAGAGTAA CAGCAACATT GCAAATTTAT AAAGGGGATT TTACAGTGCC CGTTCTATTA 1560
TCACTTAGAG TTTATGGTCA AACAGGAACA CTTGCAGGGA ATCCTAGTTT TCCTTCTTTA 1620
TATGCAGCCA CATATGAAAA CACACTTTTG GGAAGAATTA GAGAGCATAT TGCTCCACCT 1680
GCTCTTTTCA GAGCCTCCAA CGCATACATT TCGAATGGCG TTCAGGCAAT TTGGAGAGGA 1740
ACAGCAACGA CGAGAGTTTC GCAAGGTCTG TATTCCGTTG TAAGAATCGA TGAAAGACCT 1800
TTAGCAGGTT ATTCAGGAGA AACAAGAACG TATTATTTAC CAGTGACACT TTCAAATTCA 1860
AGTCAAATCC TTACACCTGG TTCTTTAGGA AGTGAGATTC CAATTATCAA TCCAGTTCCG 1920
AATGCATCTT GTAAAAAGGA AAACTCGCCT ATTATCATTC ATCATGATCG AGAGAAGCAT 1980
CGTGAACGCG ATTATGATAA AGAGCATATT TGTCATGATC AAGCTGAGAA GTATGAACGC 2040
GATTATGATA AAGAATAACT AATTATGTAA GAGATTTGTA AACAAGAGAA ATAGCATTTT 2100
ACTATTTCTC TTGTTTTTAA TCTATATATA GAATGGTAGA CGCTCTTTAA ATTAAATGTA 2160
AAAAAAGGGG GCTAAGATTA TAATGAAATC AAATCCAAAA CAATATATAG CTAATTATTT 2220
TACTTCTTTT TCATGTATTG GTCCGGATTG TGAAGATCA 2259
```

( 2 ) INFORMATION FOR SEQ ID NO:8:

( i ) SEQUENCE CHARACTERISTICS:
( A ) LENGTH: 340 amino acids
( B ) TYPE: amino acid
( D ) TOPOLOGY: linear ( i i ) MOLECULE TYPE: protein ( v i ) ORIGINAL SOURCE:
( A ) ORGANISM: Bacillus thuringiensis
( B ) STRAIN: thompsoni ( x i ) SEQUENCE DESCRIPTION: SEQ ID NO:8:

```
Met Ala Ile Met Asn Asp Ile Ala Gln Asp Ala Ala Arg Ala Trp
1               5                   10                  15

Asp Ile Ile Ala Gly Pro Phe Ile Arg Pro Gly Thr Thr Pro Thr Asn
                20                  25                  30

Arg Gln Leu Phe Asn Tyr Gln Ile Gly Asn Ile Glu Val Glu Pro Gly
            35                  40                  45

Asn Leu Asn Phe Ser Val Val Pro Glu Leu Asp Phe Ser Val Ser Gln
        50                  55                  60

Asp Leu Phe Asn Asn Thr Ser Val Gln Gln Ser Gln Thr Ala Ser Phe
    65                  70                  75

Asn Glu Ser Arg Thr Glu Thr Thr Ser Thr Ala Val Thr His Gly Val
80                  85                  90                  95

Lys Ser Gly Val Thr Val Ser Ala Ser Ala Lys Phe Asn Ala Lys Ile
                100                 105                 110

Leu Val Lys Ser Ile Glu Gln Thr Ile Thr Thr Thr Val Ser Thr Glu
            115                 120                 125

Tyr Asn Phe Ser Ser Thr Thr Thr Arg Thr Asn Thr Val Thr Arg Gly
        130                 135                 140

Trp Ser Ile Ala Gln Pro Val Leu Val Pro Pro His Ser Arg Val Thr
    145                 150                 155

Ala Thr Leu Gln Ile Tyr Lys Gly Asp Phe Thr Val Pro Val Leu Leu
160                 165                 170                 175

Ser Leu Arg Val Tyr Gly Gln Thr Gly Thr Leu Ala Gly Asn Pro Ser
                180                 185                 190

Phe Pro Ser Leu Tyr Ala Ala Thr Tyr Glu Asn Thr Leu Leu Gly Arg
```

-continued

| | | | | | | | | | | | | | | | |
|---|---|---|---|---|---|---|---|---|---|---|---|---|---|---|---|
| | | 195 | | | | | | 200 | | | | | 205 | | |
| Ile | Arg | Glu 210 | His | Ile | Ala | Pro | Pro 215 | Ala | Leu | Phe | Arg | Ala 220 | Ser | Asn | Ala |
| Tyr | Ile 225 | Ser | Asn | Gly | Val | Gln 230 | Ala | Ile | Trp | Arg | Gly 235 | Thr | Ala | Thr | Thr |
| Arg 240 | Val | Ser | Gln | Gly | Leu 245 | Tyr | Ser | Val | Val | Arg 250 | Ile | Asp | Glu | Arg | Pro 255 |
| Leu | Ala | Gly | Tyr | Ser 260 | Gly | Glu | Thr | Arg | Thr 265 | Tyr | Tyr | Leu | Pro | Val 270 | Thr |
| Leu | Ser | Asn | Ser 275 | Ser | Gln | Ile | Leu | Thr 280 | Pro | Gly | Ser | Leu | Gly 285 | Ser | Glu |
| Ile | Pro | Ile 290 | Ile | Asn | Pro | Val | Pro 295 | Asn | Ala | Ser | Cys | Lys 300 | Lys | Glu | Asn |
| Ser | Pro 305 | Ile | Ile | Ile | His | His 310 | Asp | Arg | Glu | Lys | His 315 | Arg | Glu | Arg | Asp |
| Tyr 320 | Asp | Lys | Glu | His | Ile 325 | Cys | His | Asp | Gln | Ala 330 | Glu | Lys | Tyr | Glu | Arg 335 |
| Asp | Tyr | Asp | Lys | Glu 340 | | | | | | | | | | | |

( 2 ) INFORMATION FOR SEQ ID NO:9:

( i ) SEQUENCE CHARACTERISTICS:
( A ) LENGTH: 308 amino acids
( B ) TYPE: amino acid
( D ) TOPOLOGY: linear ( i i ) MOLECULE TYPE: protein ( v i ) ORIGINAL SOURCE:
( A ) ORGANISM: Bacillus thuringiensis
( B ) STRAIN: thompsoni ( x i ) SEQUENCE DESCRIPTION: SEQ ID NO:9:

| | | | | | | | | | | | | | | | |
|---|---|---|---|---|---|---|---|---|---|---|---|---|---|---|---|
| Met 1 | Asn | Phe | Asn | Asn 5 | Ile | Thr | Gly | Asn | Phe 10 | Lys | Asp | Val | Thr | Glu 15 | |
| Leu | Phe | Thr | Asp | Tyr 20 | Ala | Asn | Gln | Trp | Ser 25 | Arg | Gln | Asn | Gly | Gly 30 | Gly |
| Lys | Pro | Glu | Ile 35 | Ser | Leu | Ile | Val | Pro 40 | Gly | Tyr | Glu | Ala | Tyr 45 | Ala | Val |
| Thr | Ser | Ser 50 | Asp | Asp | Arg | Thr | Ile 55 | Tyr | His | His | Pro | Lys 60 | Lys | Lys | Lys |
| Arg | Glu 65 | Lys | Ser | Arg | Ser | His 70 | His | Gly | Cys | Ser | Ser 75 | Glu | Asn | Gln | Glu |
| Arg 80 | Ile | Tyr | Glu | Asp | Thr 85 | Tyr | Glu | Thr | Asn | Leu 90 | Ser | Phe | Asn | His | Asp 95 |
| Pro | Asn | Leu | Met | Glu 100 | Glu | Cys | Glu | Lys | Glu 105 | Ile | Glu | Leu | Ala | Thr 110 | Glu |
| Thr | Tyr | Glu | Asn 115 | Ala | Ser | Cys | His | Glu 120 | Lys | Lys | Ile | Lys | Ile 125 | Gln | Ile |
| Gly | Gly | Asn 130 | Val | Glu | Asn | Tyr | Gly 135 | Glu | Trp | Phe | Val | Tyr 140 | Glu | Gly | Ala |
| Thr | Leu 145 | Ser | Gly | Lys | Asp | Leu 150 | Leu | Ser | Ile | Asp | Val 155 | Phe | Gly | His | Glu |
| Pro 160 | Val | Asp | Ile | Asp | Gln 165 | Val | Pro | Val | Ser | Leu 170 | His | Pro | Gly | Glu | Ile 175 |
| Glu | Val | Leu | Lys | Arg 180 | Pro | Leu | Glu | Val | Asp 185 | Thr | Tyr | Arg | Ser | Tyr 190 | Lys |
| Ile | Arg | Pro | Arg | Ser | Lys | Val | Thr | Ala | Thr | Leu | Lys | Val | Lys | Gln | Lys |

-continued

| | | | | | | | | | | | | | | | |
|---|---|---|---|---|---|---|---|---|---|---|---|---|---|---|---|
| | | | 195 | | | | | 200 | | | | | 205 | | |
| His | Phe | Lys | Gln | Cys | Phe | Asp | Val | Glu | Thr | Asp | Val | Ser | Gly | Tyr | Val |
| | | 210 | | | | | 215 | | | | | 220 | | | |
| Ala | Ile | Ile | Gln | Lys | Gln | Lys | Asp | Cys | Asp | Val | Gln | Thr | Ser | Phe | His |
| | 225 | | | | | 230 | | | | | 235 | | | | |
| His | Val | Ala | Ala | Ile | Leu | Gln | Arg | Tyr | Tyr | Ser | Pro | Phe | Ile | Arg | Ile |
| 240 | | | | | 245 | | | | | 250 | | | | | 255 |
| Asn | Gly | Asp | Glu | Val | Thr | Leu | Leu | Cys | Lys | Gly | Val | Phe | Lys | Gly | Val |
| | | | | 260 | | | | | 265 | | | | | 270 | |
| Lys | Ile | Thr | Asp | Ile | Tyr | Ile | His | Ile | Gln | Ile | Glu | Ser | Leu | Asp | Ile |
| | | | 275 | | | | | 280 | | | | | 285 | | |
| Pro | Gly | Leu | Ile | Glu | Glu | Tyr | Asn | Ile | Tyr | Asp | Val | Asn | Gln | Arg | Asn |
| | | 290 | | | | | 295 | | | | | 300 | | | |
| Ile | Gly | Val | Met | Glu | | | | | | | | | | | |
| | 305 | | | | | | | | | | | | | | |

CRYSTAL PROTEINS OF *BACILLUS THURINGIENSIS*, GENES ENCODING THEM, AND HOST EXPRESSING THEM

Some aspects of this invention are supported by work that was funded under NIH grant number 5ROI GM 20784-17.

This application is a continuation-in-part of U.S. Ser. No. 07/817,915 (filed Jan. 10, 1992), now abandoned.

FIELD OF THE INVENTION

The present invention is directed to two crystal proteins of *Bacillus thuringiensis* having insecticidal activity, the genes which encode them, and hosts expressing them.

BACKGROUND OF THE INVENTION

During sporulation, *Bacillus thuringiensis* (hereafter B.t.) produces proteinaceous crystals which are lethal to a variety of insect larvae. The proteins contained in the crystal, after being ingested by susceptible insect larvae, are transformed into biologically active moieties by proteases present in the insect gut. The crystal proteins are highly potent at destroying the gut's epithelium, and even nanogram amounts are capable of killing susceptible larvae. Some of the major insect pests in agriculture and forestry are species of the order Lepidoptera, which are known to be susceptible to B.t. toxins.

These crystal proteins have been grouped into four classes based on their host range and sequence homologies: Lepidoptera-specific (I), Lepidoptera/Diptera-specific (II), Coleoptera-specific (III), and Diptera-specific (IV) (Höfte, H. and H. R. Whiteley 1989. "Insecticidal Crystal Proteins of *Bacillus thuringiensis*." *Microbiol. Rev.* 53:242–255). Significant amino-acid similarities exist between the crystal proteins of the different classes with the carboxy-terminal half of the crystal proteins containing most of the conserved sequences. Five well-defined regions are conserved among most of the known crystal proteins; these are located in the N-terminal half of the protein, which is responsible for toxicity (Höfte, H. and H. R. Whiteley. 1989. "Insecticidal Crystal Proteins of *Bacillus thuringiensis*." *Microbiol. Rev.* 53:242–255). One exception is CytA, a 28 kDa cytolytic toxin from *B. thuringiensis* subsp. *israelensis* which has no detectable sequence identity with the other crystal proteins (Höfte, H. and H. R. Whiteley. 1989. "Insecticidal Crystal Proteins of *Bacillus thuringiensis*." *Microbiol. Rev.* 53:242–255).

The majority of the crystal proteins and all Class I lepidopteran-specific crystal proteins are synthesized as 130–140 kDa protoxins, which are then proteolytically cleaved in the insect midgut to 65–70 kDa active toxins. Some crystal proteins, Classes II and III, are produced as 65–70 kDa toxins. The only crystal protein which falls outside these two size ranges is CytA, one of five crystal proteins from dipteran-specific *Bacillus thuringiensis subsp. israelensis*. However, CytA has a different mode of action from other crystal proteins (Thomas, W. E., and D. J. Ellar. 1983. "Mechanism of action of *Bacillus thuringiensis var. israelensis* insecticidal δ-endotoxin." FEBS Lett. 154:362–367) and also has recently been reported to not be essential for mosquitocidal activity (Delecluse et al. 1991. "Deletion by in vivo recombination shows that the 28-kilodalton cytolytic polypeptide from *Bacillus thuringiensis subsp. israelensis* is not essential for mosquitocidal activity." *J. Bacteriol.* 173:3374–3381).

SUMMARY OF THE INVENTION

The present invention results from the identification of a unique crystalline insect toxin produced by B.t. subsp. thompsoni. The crystalline insect toxin comprises two unique polypeptides which are distinct from other B.t. proteins because of their size (electrophoretic mobilities of 40 kDa and 34 kDa), and particularly, because their deduced amino-acid sequences do not contain any of the conserved regions observed in other characterized B.t. crystal proteins. The two genes encoding these unique polypeptides were cloned and expressed in *E. coli*. The 34 kDa polypeptide has insecticidal activity in the presence or absence of the 40 kDa polypeptide, and thus, may be used alone as an insecticide. While the 40 kDa protein appears to have no insecticidal activity against the tested lepidopteran species *Manduca sexta, Artogeid rapae, Heliothis virescens*, and *Trichoplusid ni*), it may have a role in crystal formation because the naturally-occurring *B.t. thompsoni* crystals contain both proteins, and thus, may be used in combination with the 34 kDa protein as an insecticide.

Because of the relatively small length of the genes encoding these polypeptides, achieving their expression in plants should be easier than achieving expression of the other types of B.t. toxins. Additionally, the construction and expression of chimaeric B.t. toxins will be facilitated by the small size of these genes. Chimaeric toxins can be used to expand the host range of a specific toxin and decrease the likelihood that insect resistance will develop.

BRIEF DESCRIPTION OF THE FIGURES

FIG. 4: Nucleotide and deduced amino-acid sequences of the 40 kDa and 34 kDa crystal protein genes. Ribosome-binding sites are underlined twice and the inverted repeats which form a potential transcription terminator are marked by long arrows under the sequence.

DETAILED DESCRIPTION OF THE INVENTION

Figure 1A:
FIG. 1: Electron micrographs of crystals from *B.t. thompsoni*. (A) Thin-section of a sporulating *B.t. thompsoni* cell containing a crystalline inclusion. (B) Three-dimensional view of a *B.t. thompsoni* crystal. The bar in each panel represents 100 nm.

In one embodiment, the present invention is a unique crystalline insect toxin produced by B.t., comprising two polypeptides having electrophoretic mobilities of about 34 kDa and 40 kDa. In particular, the present invention is directed to the two crystal polypeptides of B.t. subspecies thompsoni having electrophoretic mobilities of around 34 kDa and 40 kDa. As mentioned above, the 34 kDa protein may be used alone as an insecticide or in combination with the 40 kDa protein. Another embodiment of the present invention is the two genes encoding these proteins. Also, the present invention is directed to probes used to isolate the genes. Still another embodiment is a recombinant DNA expression vector containing one or both of the genes encoding the two proteins. In addition, the present invention includes hosts transformed by a recombinant DNA expression vector containing one or both genes. Finally, the present invention is directed to a process for producing the novel proteins using a host transformed with a recombinant DNA expression vector containing the genes.

It is known that conservative substitutions of amino acids in proteins can be made without significantly affecting biological activity, resulting in a homologous sequence which retains its insecticidal activity. For example, structurally related amino acids (such as Asp and Glu) may be substituted for each other. The insecticidal activity of such homologous sequences may be readily determined using the routine insect toxicity assay described in Example 1 below. Further, as a result of the degeneracy of the genetic code, it is possible to generate a variety of nucleotide sequences through mutagenic or DNA-synthesizing techniques which are capable of encoding the same amino acid sequence. Such obvious modifications to the proteins and their underlying DNA sequences are considered to be within the scope of the present invention.

Suitable host cells include prokaryotes and eukaryotes. Preferred prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Cyanobacteria, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Suitable eukaryotes include fungi such as Phycomycetes and Ascomycetes, which include yeast, such as Saccharomyces and Schizosaccharomyces; and Basidiomycetes yeast, such as Rhodotorula, Aureobasidium, Sporobolomyces, and the like. Two particularly preferred hosts are *E. coli* DH5α and JM103.

Suitable expression vectors include those which are functional in a selected host. Examples of such vectors are pBR322, pACYC184, pPL703E, RSF1010, pRO1614, pBluescript II SK+/-, pBluescript II KS+/-, and pKK223-3. Of those, pKK223-3 is a preferred expression vector.

The expression vector may include any of various transcriptional regulatory regions, such as regions of the trp gene, lac gene, gal gene, the lambda left and right promoters, the Tac promoter, or the naturally-occurring promoters associated with the two genes.

The present invention is described more fully by the example below, although it is in no way limited to this particular example.

EXAMPLE 1

*B.t. thompsoni* was obtained from P. Baumann, University of California, Davis (originally from H. D. Burges with the Dulmage designation HD-542). *B.t. kurstaki* HD-1 Dipel was obtained from L. A. Bulla (Kronstad et al. 1983. "Diversity of locations for *Bacillus thuringiensis* crystal protein genes." *J. Bacteriol.* 154:419–428). *E. coli* DH5α (Bethesda Research Laboratories) and JM103 were the hosts for cloning purposes. *E. coli* DPWC and JGM (obtained from Melvin Simon via Kelly Hughes) were used for γδ mobilization. Plasmids pTZ18R (Pharmacia) and pBluescript II KS+ (Stratagene) were used as cloning vectors. Plasmid pKK223-3 (Pharmacia) was used as an expression vector for the crystal protein genes.

Molecular methods and enzymes

The standard molecular methods used have been described previously (Sambrook et al. 1989. "Molecular cloning: a laboratory manual," 2nd ed. Cold Spring Harbor Laboratory, Cold Spring Harbor, N.Y.). *B.t. thompsoni* plasmid DNA was isolated as described previously (Kronstad et al. 1983. "Diversity of locations for *Bacillus thuringiensis* crystal protein genes." *J. Bacteriol.* 154:419–428) and purified by CsCl gradient centrifugation. *E. coli* plasmid DNA was isolated by the method of Birnboim and Doly (1979. "A rapid alkaline extraction procedure for screening recombinant plasmid DNA." *Nucleic Acids Res.* 7:1513–1523). *E. coli* transformation was by electroporation (Dower et al. 1988. "High efficiency transformation of *E. coli* by high voltage electroporation." *Nucleic Acids Res.* 16:6127–6145) or with competent cells (Sambrook et al. 1989. "Molecular cloning: a laboratory manual," 2nd ed. Cold Spring Harbor Laboratory, Cold Spring Harbor, N.Y.). Restriction enzymes were purchased from New England BioLabs. Inc., Boehringer-Mannheim, and Bethesda Research Laboratories. Calf intestinal alkaline phosphatase came from Boehringer-Mannheim. Klenow fragment, exonuclease III and reverse transcriptase were purchased from Bethesda Research Laboratories. All enzymes were used according to the instructions of the manufacturers.

Electron microscopy

A synchronized culture of *B.t. thompsoni* was grown at 30° C. until the presence of phase-dark prespores and the formation of crystalline inclusions were observed by phase-contrast microscopy. The cells were harvested by centrifugation and resuspended in 0.1M cacodylate buffer, pH 7.3. The cells were fixed with 3% glutaraldehyde and resuspended in 1.5% Noble agar. The agar-embedded cells were washed in cacodylate buffer and dehydrated with ethanol. Finally, the cells were washed with propylene oxide and infiltrated and embedded in plastic resin. After thin-sectioning, the samples were viewed by scanning electron microscopy. Purified *B.t. thompsoni* crystals were prepared as above, but viewed by transmission electron microscopy.

*B.t. thompsoni plasmid DNA hybridization*

Plasmids were isolated from *B.t. thompsoni* and *B.t. kurstaki* HD-1 Dipel, separated in a 0.6% horizontal agarose gel and transferred to nitrocellulose as described previously (Kronstad et al. 1983. "Diversity of locations for *Bacillus thuringiensis* crystal protein genes. "*J. Bacteriol.* 154:419–428). A DNA fragment specific to the 40 kDa and 34 kDa genes was radiolabelled by hexanucleotide random priming (Feinbert et al. 1983. "A technique for radiolabeling DNA restriction endonuclease fragments to high specific activity." *Anal. Biochem.* 132:6–13). The radiolabelled DNA was subjected to alkaline denaturation and allowed to hybridize to the Southern blot DNA in 20% formamide, 3X SSC (1X SSC is 0.15M NaCl plus 0.015M sodium citrate) for 20 h 25° C. The blot was washed in 2X SSC, 0.1% sodium dodecyl sulfate (SDS) for 15 min at 25°, 37°, and 42° C., air-dried and exposed to Kodak XAR film.

Antibody production and N-terminal sequencing

Crystals were isolated from *B.t. thompsoni* and purified by Renografin gradient centrifugation. The purified crystals were solubilized in 4% SDS/10% B-mercaptoethanol and electrophoresed in a preparative 10% SDS-polyacrylamide gel. The peptide bands were visualized by staining in 0.15M potassium chloride and the individual protein bands were excised from the gel. The proteins were eluted from the polyacrylamide gel slices at 4° C. with 4 Watts constant power for 3 h by using the ISCO electroelution-concentration device. The protein concentration of the samples was determined by the method of Bradford (1976. "A rapid and sensitive method for the quantitation of microgram quantities of protein utilizing the principle of protein-dye binding." *Anal. Biochem.* 72:248–254). Each sample, containing 20 μg of protein in 0.5 ml 10 mM Tris/1 mM EDTA, was emulsified 1:1 with Freund's Complete adjuvant and injected into mice subcutaneously (Herbert, W. J. 1968. "The mode of action of mineral-oil emulsion adjuvants on antibody production in mice." Immun. 14:301–318). Five weeks later a booster of 10 ng of each sample was administered intramuscularly and ascites sarcoma 180/TG cells were injected into the mice intraperitoneally. The polyclonal antiserum was harvested from the ascites fluid 10–14 days later and was centrifuged to obtain a clarified supernatant and used without further purification.

*B.t. thompsoni* crystals were purified and electrophoresed as above and transferred to an Immobilon membrane (Millipore). The N-terminal amino-acid sequences of the 40 kDa and 34 kDa crystal proteins were determined by automated Edman degradation.

Crystal protein gene cloning

Based on the amino-acid sequences, two degenerate DNA oligonucleotides were synthesized: a 38-mer for the 40 kDa crystal protein, 5'-ATG AA (C,T) TTC AAC AA(C,T) AT(C,T) ACI GGI AAC TT(C,T) AAG GAG GT-3', SEQ ID No. 1, and a 32-mer for the 34 kDa crystal protein, 5'-ATG AAT GA(C,T) AT(-T,A) GCI CA(G,A) GAT GCI GCI (C,A)GI GC-3'SEQ ID No. 2. Deoxyinosine was used as a neutral base at the fourfold redundant positions to reduce base mismatching. *B.t. thompsoni* plasmid DNA was digested with EcoRI and subjected to sucrose gradient centrifugation. Fractions were separated by agarose gel electrophoresis, transferred to nitrocellulose and hybridized to both oligonucleotides. Probe-reactive fractions were ligated into pTZ18R (which had been digested with EcoRI and treated with calf intestinal alkaline phosphatase), and transformed into *E. coli* DH5α. Positive clones were selected by colony blot hybridization with the 38-mer and 32-mer oligonucleotides and by the production of proteins reacting with the 40 kDa and 34 kDa antibodies. Two clones were selected, both of which contained the same 8.4-kb fragment but in opposite orientations, as indicated by restriction enzyme mapping (data not shown). One of the clones, pKB100, was subcloned by removing an SstI-SstI fragment from the 5'-end and ligating the 7.5-kb SstI-EcoRI fragment into pTZ18R, generating pKB102.

Subclone Construction

Recombinant plasmid pKB102 was used to generate the subclones pKB107 and pKB109. pKB102 was digested with BstEII followed by digestion with exonuclease III and treatment with S1 nuclease to generate blunt ends that were ligated to yield pKB107. To generate pKB109, the transposon γδ was mobilized by bacterial mating into an SstI-NruI subclone of pKB102 (see FIG. 3).

To obtain specific clones of the genes encoding the 40 kDa and 34 kDa crystal proteins, the polymerase chain reaction (PCR) was used to isolate their respective sequences. The priming oligonucleotides were used to amplify the 40 kDa coding region (with the introduction of an ApaI site upstream and a SalI site downstream) and also the 34 kDa coding region (with the introduction of a SmaI site upstream and a XbaI site downstream). The sequences of the PCR primers were as follows: for the gene encoding the 40 kDa protein, sense strand 5'-GAG GGC CCA ATA AGG TGT CAG CT-3' and its nonsense strand 5'-GCG TCG ACT ATC ATT CCA TTA CAC-3'; for the gene encoding the 34 kDa protein, sense strand 5'-CTC CCG GGT GTA ATG GAA TGA TA-3' and its nonsense strand 5'-GCT CTA GAT CTT CAC AAT CCG GA-3'. Amplification was performed in 100 μl reaction volume containing 5 ng template, 1 μg of each primer, 200 μM dNTP's, 2.5 U Tag DNA Polymerase (Promega) and Tag buffer. The thirty-two rounds of amplification consisted of 15s at 94° C., 15s at 45° C., and 60s at 72° C. in a Coy thermal cycler.

The PCR-generated fragments were digested with the appropriate restriction enzymes and cloned into pBluescript II KS+ to generate pKB401 (40 kDa) and pKB341 (34 kDa). Expression vectors were then constructed by excising the 40 kDa and 34 kDa genes as a 997-bp KpnI(blunt)-HindIII fragment and a 1300-bp PstI-SstI(blunt) fragment, respectively from these plasmids and ligating them into pKK223-3, generating pKB200 and pKB201. To generate a subclone containing both crystal protein genes, the 40 kDa gene was excised from pKB200 as a EcoRI-HindIII(blunt) fragment and ligated into pKB201 digested with EcoRI-PstI(blunt) generating, pKB202.

DNA Sequencing

Both strands of the DNA were sequenced using the dideoxy-chain termination method of Sanger et al. (1977. "DNA Sequencing with chain-terminating inhibitors." *Proc. Natl. Acad. Sci. USA.* 74:5463–5467). DNA fragments from pKB102 were subcloned into pTZ18R and successive unidirectional deletions were created using exonuclease III. The second strand and any gaps in the first strand were sequenced using a series of complementary synthetic oligonucleotides. Sequencing templates were generated by subjecting CsCl-purified plasmid DNA to alkaline denaturation followed by ethanol precipitation. Sequencing was accomplished using [$\alpha$-$^{35}$S]dATP (New England Nuclear) and the Sequenase Version 2.0 kit (US Biochemical). Sequence similarities were analyzed with FASTDB from the IntelliGenetics software package. The sequence data disclosed herein has been assigned the accession number in GenBank of M76442.

Insect toxicity assays

Toxicity of purified *B.t. thompsoni* crystals and *E. coli* inclusions to neonate larvae of the tobacco hornworm, *Manduca sexta*, was tested as described previously except that the crystals and/or inclusions were not solubilized prior to the assay (Schnepf et al. 1990. "Specificity-determining regions of a lepidopteran-specific insecticidal protein produced by *Bacillus thuringiensis*." *J. Biol. Chem.* 265:20923–20930). Protein concentrations were estimated by densitometry (202 Ultrascan laser densitometer; LKB Instruments, Inc.) of Coomassie-blue stained SDS-polyacylamide gels with dilutions of bovine $\gamma$ globulin used as standards.

Crystal structure

Figure 1B:

To determine the shape of *B.t. thompsoni* crystals, cells were grown until phase-dark prespores and crystals were observed. The electron micrograph of a thin-sectioned cell (FIG. 1A) showed the production by *B.t. thompsoni* of a square crystal alongside the spore. To determine whether the crystals were flat or cuboidal, purified *B.t. thompsoni* crystals were viewed by transmission electron microscopy. The electron micrograph in FIG. 1B showed the three-dimensional structure of a *B.t. thompsoni* crystal as cuboidal rather than flat.

Cloning of the *B.t. thompsoni* genes in *E. coli*

Figure 2A:
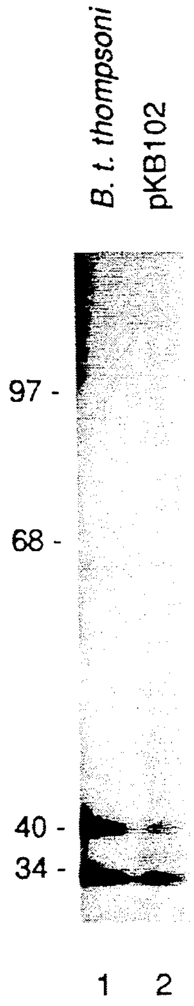
FIG. 2: Electrophoretic analysis of crystals and inclusions from recombinant *E. coli* clones. (A) Coomassie-blue stained gel of purified *B.t. thompsoni* crystals (lane 1) and purified inclusions from *E. coli* clone pKB102 (lane 2). (B) Immunoblot with antibody specific for the 40 kDa crystal protein (lane 1, *B.t. thompsoni* crystals; lanes 2-7, purified *E. coli* inclusions: lane 2, pKB102; lane 3, pKB107; lane 4, pKB109; lane 5, pKB200; lane 6, pKB201; lane 7, pKB202. (C) Immunoblot with antibody specific for the 34 kDa crystal protein (lane designations are the same as in panel B). The *E. coli* DH5α was the host for the plasmids pKB102 and pKB107, while *E. coli* JGM was the host for pKB109 and *E. coli* JM103 was the host for pKB200, pKB201, and pKB202.
Figure 2B:
Figure 2C:

Electrophoretic analysis of purified *B.t. thompsoni* crystals showed only two peptide bands which migrated at estimated electrophoretic mobilities of 40,000 and 34,000 daltons (FIG. 2A, lane 1). Immunoblots showed the specificity of the two crystal protein antibody preparations (FIGS. 2B and 2C, lane 1). Additionally, these two antibodies did not cross-react with representative members from each of the four crystal protein classes or with CytA (data not shown).

To facilitate cloning of the *B.t. thompsoni* crystal proteins, the N-terminal sequence was determined for the 40 kDa polypeptide, MNFNNITGNFKD-VTELFTDYANQX (S) XQNG, SEQ ID No. 9 and the 34 kDa polypeptide AIMNDIAQDAARAX-DIIAGPFIRPGT (T) PXN (N) QLF (N) (Y) X(I) (G) (N). SEQ ID No. 8 . Residues in parentheses are uncertain and unknown residues are represented with an X. From these amino-acid sequences, DNA oligonucleotides were synthesized. Both oligonucleotides hybridized to a 7.5-kb SstI-EcoRI fragment cloned from *B.t. thompsoni* plasmid DNA as described above. Recombinant *E. coli* carrying pKB102 (FIG. 3), synthesized two polypeptides which reacted with the 40 kDa and 34 kDa antibodies, respectively (FIGS. 2B and C, lane 2). The mobilities of the polypeptides produced from pKB102 were identical or very similar to those polypeptides present in preparations of purified *B.t. thompsoni* crystals (FIG. 2A, lanes 1 and 2). A ca. 100 kDa peptide was visible in immunoblots of *B.t. thompsoni* and pKB102 which cross-reacted with both antibody preparations (FIGS. 2B and C, lanes 1 and 2). This peptide species is possibly an aggregate of the 40 kDa and 34 kDa crystal proteins, or might represent another polypeptide present on the DNA cloned in pKB102 which cross-reacts with both antibody preparations.

Sequence determination of the cloned crystal protein genes

Figure 3:
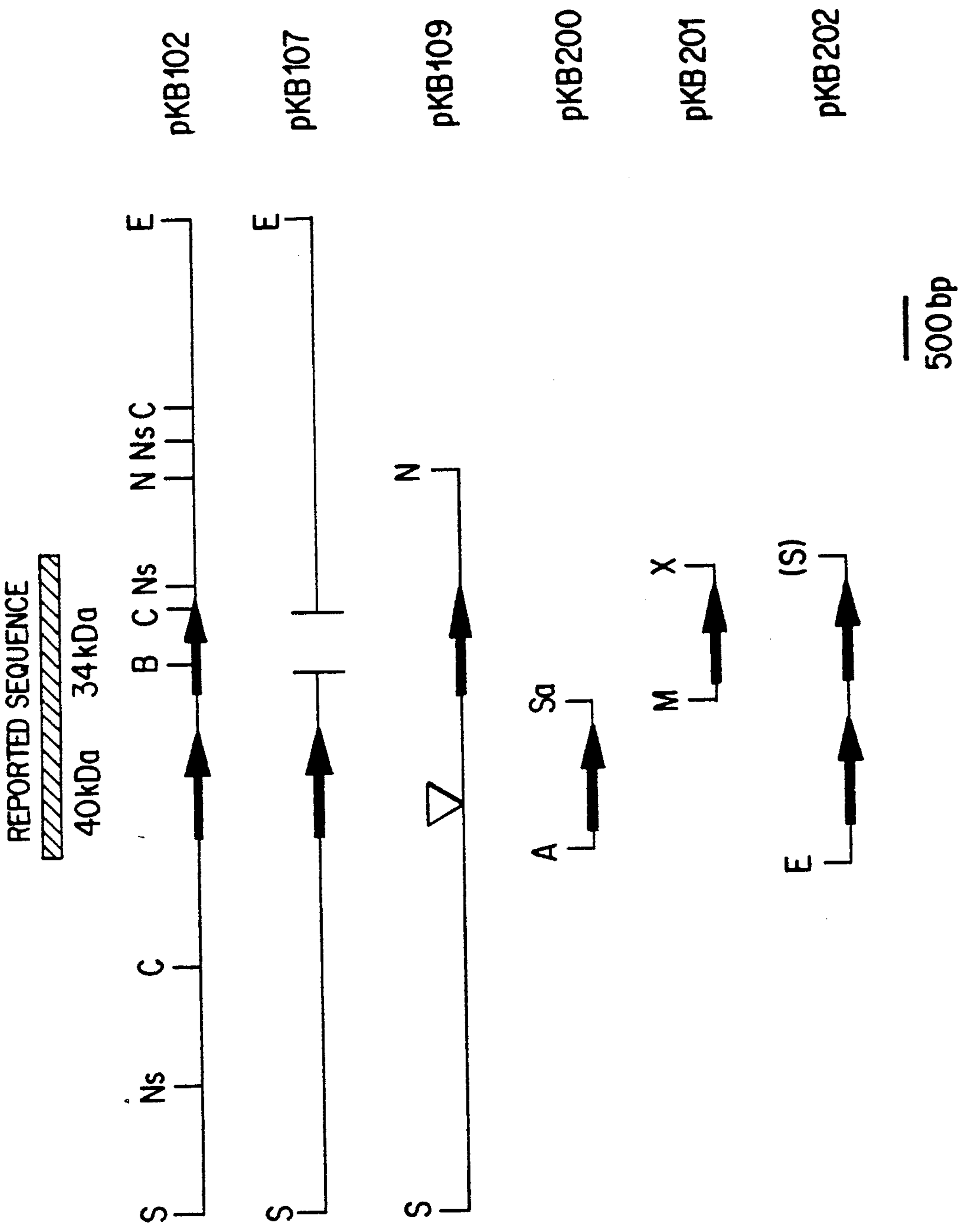
FIG. 3: Restriction maps showing the location of the crystal protein genes on the recombinant plasmids used in this study. The positions and orientations of the two crystal protein genes are indicated by arrows. The open area in pKB107 is a deleted region. The black triangle in pKB109 is the site of δ insertion. The diagramed size of pKB109 does not account for the additional 5.7 kb of δ DNA. The following abbreviations were used for restriction sites: A, ApaI; B, BstEII; C, ClaI; E, EcoRI; H, *Hind*III; M, *Sma*I; N, *Nru*I; Ns, *Nsi*I; S, *Sst*I; Sa, *Sal*I; X, *Xba*I. The restriction sites shown on pKB200 and pKB201 were obtained from PCR-amplification. The *Sst*I site in parentheses on pKB202 was lost during cloning.

The region of pKB102 containing the genes encoding the 40 kDa and 34 kDa crystal proteins was sequenced (FIG. 3). The DNA sequence (FIG. 4) revealed the presence of two open reading frames in the same orientation and separated by 64 nucleotides, with each open reading frame preceded by a potential ribosome-binding site. The sequence of the first open reading frame matched the N-terminal amino-acid sequence of the 40 kDa protein determined previously, and could encode a polypeptide with a predicted molecular mass of 35,384 daltons. The N-terminal amino-acid sequence predicted from the sequence of the second open reading frame corresponded to the N-terminal amino-acid sequence of the 34 kDa protein. This ORF could code for a polypeptide with a predicted molecular mass of 37,505 daltons. Since both strands of the DNA were sequenced, the discrepancies between the predicted molecular masses of the two crystal proteins and those estimated by electrophoretic mobility most likely resulted from anomalous migration during electrophoresis. Molecular mass discrepancies have also been observed for CryIIA and CryIIB: each sequence predicts a size of ca. 71 kDa, but the proteins migrate as 65 kDa and 50 kDa, respectively.

The sequences were searched for any regions that resembled *B. thuringiensis, Bacillus subtilis* or *E. coli* promoter structures. No likely promoter sequences were found in the sequenced region, either in the region between the two genes or for approximately 700 nucleotides upstream of the 40 kDa crystal protein gene.

The sequenced region was searched for the presence of inverted repeat structures which could result in transcription termination. A sequence which could serve as a Rho-independent transcriptional terminator was found downstream of the 34 kDa gene. Transcription of this region could lead to the formation of a stem-and-loop structure with a $\Delta G°$ of $-19.1$ kcal, calculated according to the rules of Tinoco (1973. "Improved estimation of secondary structure in ribonucleic acids." Nature. (London) New Biol. 246:40–41). However, this inverted repeat structure does not have the classical GC-rich region of other terminators or a run of T's after the stem-and-loop, thus this structure may not serve to terminate transcription. The organization of the two ORFs, the presence of individual ribosome-binding sites, the lack of a promoter between the two genes, and the putative transcription terminator suggest that these genes are likely to be part of an operon. This operon may have additional ORFs upstream of the 40 kDa crystal protein gene and possibly downstream of the 34 kDa crystal protein gene as well.

The predicted amino-acid sequences of the two ORFs were analyzed to identify any similarities to other known protein sequences. No statistically significant similarities were detected for the 40 kDa or 34 kDa crystal proteins to any protein sequence, including any other sequenced crystal protein. Additionally, comparison of the 40 kDa and 34 kDa amino-acid sequences showed no substantial regions of identity between the two proteins.

Plasmid profile

Figure 5:
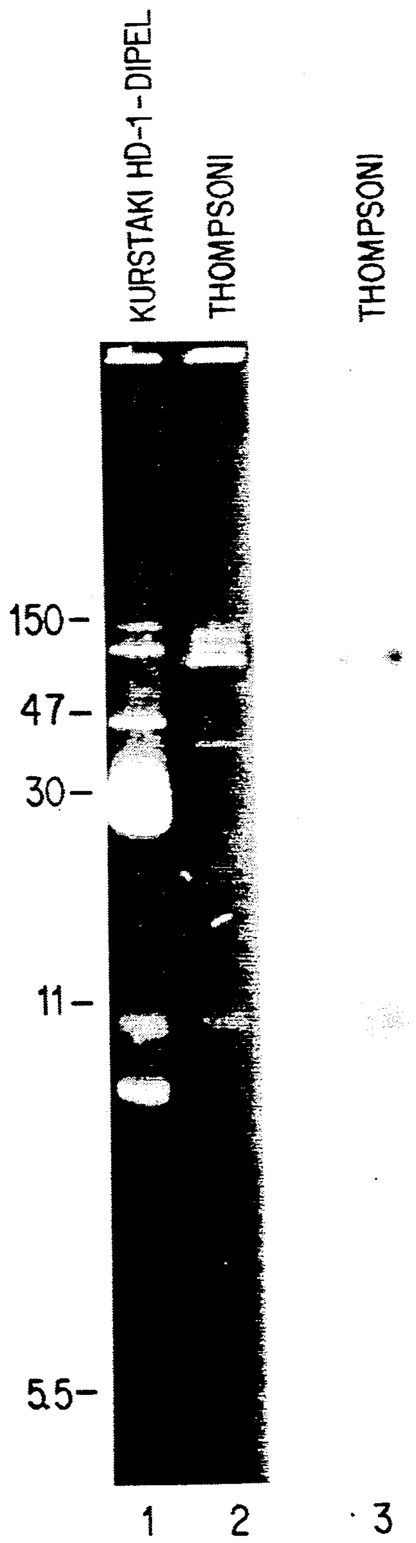
FIG. 5: Electrophoretic analysis of plasmids and location of crystal protein genes in *B.t. thompsoni*. Lanes 1 and 2: agarose gel stained with ethidium bromide of plasmids isolated from HD-1-Dipel (lane 1) and *B.t. thompsoni* (lane 2). The numbers on the left indicate size in MDa. Lane 3: autoradiograph of lane 2 DNA transferred to nitrocellulose and hybridized with a 32P-labelled fragment from the region encoding the *B.t. thompsoni* crystal protein genes. The black dot to the right of lane 2 indicates the plasmid carrying the crystal protein genes. Some hybridization was observed with the linearized fragments, which most likely resulted from shearing of the crystal protein gene-containing plasmid.

To examine the plasmid profile of *B.t. thompsoni*, purified plasmids were separated in an agarose gel. The sizes of the *B.t. thompsoni* plasmids were determined by comparison with sized plasmids isolated from *B. thuringiensis* HD-1-Dipel (FIG. 5, lanes 1 and 2). Five plasmids were observed in *B.t. thompsoni* ranging from 40 MDa to greater than 150 MDa with four of the plasmids clustered around 100 to 150 MDa (FIG. 5A, lane 2).

To determine which plasmid encoded the crystal protein genes, *B.t. thompsoni* plasmid DNA was transferred to nitrocellulose and hybridized with a radioactive probe specific to the 40 kDa and 34 kDa genes. The crystal protein genes were located on the predominant plasmid species of ~100 MDa (FIG. 5, lane 3). This observation agrees with the results of Carlton and Gonzalez (1984. "Plasmid-associated delta-endotoxin production in *Bacillus thuringiensis*," pages 387–400. In A. T. Ganesan and J. A. Hoch (eds.), *Genetics and biotechnology of bacilli*. Academic Press, New York), who showed that an acrystalliferous strain of *B.t. thompsoni* resulted from the loss of a 100 MDa plasmid.

Description of subclone constructions

As described above, subclones of pKB102 were generated in which the gene expression of each crystal protein was individually eliminated. Insertional inactivation or deletion were used, in order to leave any regulatory elements on pKB102 intact. Because of the lack of unique restriction enzyme sites within the 40 kDa gene, $\gamma\delta$ transposition was used to inactivate the expression of its gene product. Plasmid pKB109 (FIG. 3) had a $\gamma\delta$ insertion in the 40 kDa crystal protein gene after nucleotide 161 of FIG. 4, resulting in the synthesis of only the 34 kDa gene product (FIGS. 2B and C, lane 4). Though part of an operon, the 34 kDa crystal protein gene was expressed in pKB109, either because $\gamma\delta$ does not contain any transcriptional terminators or it contains a promoter which was used for transcription of the 34 kDa gene. A different approach was used to inactivate the 34 kDa crystal protein gene; a unique restriction enzyme site, BstEII, within the 34 kDa gene was used to initiate exonuclease III digestion. A resulting subclone, pKB107 (FIG. 3), had a deletion in the 34 kDa crystal protein gene from nucleotides 1190 to 1920 of FIG. 4. This clone expressed only the 40 kDa crystal protein as demonstrated by immunoblot analysis (FIGS. 2B and C, lane 3).

To determine the insecticidal activity of the crystal proteins, subclones were constructed that contained only the 40 kDa gene (pKB200), only the 34 kDa gene (pKB201), or both genes (pKB202) (FIG. 3). In these subclones, the genes were expressed under the control of the strong tac promoter. Each gene had its own Shine-Dalgarno sequence present and was cloned upstream of the *E. coli rrnB* T1 and T2 terminators to insure transcriptional termination. Recombinant *E. coli* with pKB200 expressed only the 40 kDa crystal protein (FIGS. 2B and C, lane 5), whereas the subclone pKB201 synthesized only the 34 kDa crystal protein (FIGS. 2B and C, lane 6). Both crystal proteins were expressed in *E. coli* carrying pKB202 (FIGS. 2B and C, lane 7).

Insect toxicity assays

Purified *B.t. thompsoni* crystals and inclusions isolated from several recombinant *E. coli* clones were tested for toxicity to the larvae of the lepidopteran, *Manduca sexta*. The samples were not solubilized prior to testing for toxicity to insect larvae, because the various methods (pH >11 or 0.2% sarkosyl in 0.1M carbonate buffer) which were successful in solubilizing the crystals or inclusions destroyed their biological activity (data not shown). Solutions that normally solubilize other crystal proteins and inclusions (i.e. 0.1M carbonate buffer, pH 10, 0.2% $\beta$-mercaptoethanol) resulted in concentrations of soluble protein that were too low to use in the insect assays.

The recombinant *E. coli* carrying pKB102, which produced both crystal proteins, exhibited equivalent toxicity levels as the *B.t. thompsoni* crystals with 50% killing observed at 0.40 μg/cm2 (see Table 1 below). The clone, pKB202 (which has been deposited with the American Type Culture Collection at 12301 Parklawn Drive, Rockville, Md., U.S.A. and given the deposit number ATCC 68889), had an LC50 value of 0.98 μg/cm2, however, the 34 kDa polypeptide concentration was the same as *B.t. thompsoni* and pKB102 of 0.25 μg/cm$^2$. When only the 34 kDa crystal protein was expressed, in *E. coli* carrying pKB109 (which has also been deposited with the American Type Culture Collection and given the deposit number ATCC 68891) and pKB201 (which has been deposited with the American Type Culture Collection and given the deposit number ATCC 68890), the concentration of 34 kDa polypeptide at the LC50 levels were similar, 0.25 μg/cm2, to those observed in clones expressing both crystal proteins, pKB102 (which has been deposited with the American Type Culture Collection and given the deposit number ATCC 68892) and pKB202 (Table 1). However, the *E. coli* that expressed only the 40 kDa crystal protein, clones carrying pKB107 and pKB200, were not toxic to the larvae at concentrations of 3 μg/cm$^2$ (Table 1). *B.t. thompsoni* crystals also demonstrated toxicity against the lepidopteran, Artogeia rapae (Cabbage white), but did not kill larvae of *Heliothis virescens* or *Trichoplusia ni* at concentrations of 3 μg/cm$^2$ (concentration of both crystal proteins), although growth of these larvae was severely stunted. Purified *B.t. thompsoni* crystals were also tested for toxicity to the dipteran, *Aedes aegypti*, and the coleopteran, *Leptinotarsa decemlineata* (Colorado potato beetle), but no toxicity was observed.

TABLE 1

| Assay for toxicity of *B.t. thompsoni* crystals and inclusions purified from recombinant *E. coli* strains. | | | |
|---|---|---|---|
| Organism or clone | Expressed gene(s) (kDa)[a] | $LC_{50}$[b] for *M. sexta* | 34-kDa concn[c] |
| *B.t. thompsoni* | 40, 34 | 0.40 | 0.25 |
| pKB102 | 40, 34 | 0.40 | 0.25 |
| pKB107 | 40 | >3.0 | |
| pKB109 | 34 | 0.25 | 0.25 |
| pKB200 | 40 | >3.0 | |
| pKB201 | 34 | 0.25 | 0.25 |
| pKB202 | 40, 34 | 0.98 | 0.25 |

[a]The molecular mass in kilodaltons of the protein which the gene encodes.
[b]$LC_{50}$ values (in micrograms per square centimeter ± 50%) are based on total concentration of expressed polypeptide(s). Protein concentrations were estimated as described above.
[c]Estimated protein concentration (in micrograms per square centimeter ± 50%) of the 34-kDa polypeptide at the $LC_{50}$ values of the various clones.

We claim:

1. An isolated DNA fragment having the nucleotide sequence
   SEQ ID NO. 7,
   or an equivalent nucleotide sequence coding for the following two amino acid sequences: SEQ ID NO: 8 and SEQ ID NO: 9.
2. An isolated DNA fragment having the nucleotide sequence
   SEQ ID NO. 7, nucleotides 962-2259
   or an equivalent nucleotide sequence coding for the amino acid sequence SEQ ID NO: 8.
3. A recombinant DNA expression vector comprising an isolated DNA fragment according to claim 2.
4. A recombinant DNA expression vector according to claim 3 which is pKB201.
5. A recombinant DNA expression vector according to claim 3 which is pKB109.
6. A recombinant DNA expression vector comprising an isolated DNA fragment according to claim 1.
7. A recombinant DNA expression vector according to claim 6 which is pKB202.
8. A recombinant DNA expression vector according to claim 6 which is pKB102.
9. A host microorganism transformed by a recombinant DNA expression vector according to claim 3 or 6.
10. A transformed host according to claim 9, wherein the host is *E. coli.*
11. A transformed host according to claim 10, wherein the recombinant DNA expression vector is pKB201.
12. A transformed host according to claim 10, wherein the recombinant DNA expression vector is pKB202.
13. A transformed host according to claim 10, wherein the recombinant DNA expression vector is pKB102.
14. A transformed host according to claim 10, wherein the recombinant DNA expression vector is pKB109.
15. A method for producing an insect toxin of *Bacillus thuringiensis* wherein said method comprises
    (a) transforming a suitable host microorganism with a recombinant DNA expression vector according to claims 3 or 6,
    (b) culturing said transformed host from step (a) in a suitable culture medium, and
    (c) harvesting from the culture of step (b) an essentially pure insect toxin.
16. A method according to claim 15, wherein in step (a), the recombinant DNA expression vector is pKB201.
17. A method according to claim 15, wherein in step (a), the recombinant DNA expression vector is pKB202.
18. A method according to claim 15, wherein in step (a), the recombinant DNA expression vector is pKB109.
19. A method according to claim 15, wherein in step (a), the recombinant DNA expression vector is pKB102.
20. A method of using a host microorganism transformed by a recombinant DNA expression vector according to any one of claims 3–8 to produce an insect toxin of *Bacillus thuringiensis* comprising
    (a) culturing said transformed host in a suitable culture medium, and
    (b) harvesting from the culture of step (a) an essentially pure insect toxin.

* * * * *